United States Patent [19]

Horney et al.

[11] Patent Number: 5,549,589
[45] Date of Patent: Aug. 27, 1996

[54] FLUID DISTRIBUTION MEMBER FOR ABSORBENT ARTICLES EXHIBITING HIGH SUCTION AND HIGH CAPACITY

[75] Inventors: James C. Horney; John R. Noel, both of Cincinnati, Ohio

[73] Assignee: The Procter & Gamble Company, Cincinnati, Ohio

[21] Appl. No.: 382,817

[22] Filed: Feb. 3, 1995

[51] Int. Cl.$^6$ .................. A61F 13/15; B27J 5/00
[52] U.S. Cl. .............. 604/366; 604/370; 604/374; 604/378; 264/124
[58] Field of Search ................... 604/358, 365, 604/366, 367, 370, 374; 264/124

[56] References Cited

U.S. PATENT DOCUMENTS

| | | | |
|---|---|---|---|
| 4,425,126 | 1/1984 | Butterworth et al. | 604/366 |
| 4,500,315 | 2/1985 | Pieniak et al. | 604/379 |
| 4,513,051 | 4/1985 | Lavash | 428/212 |
| 4,537,590 | 8/1985 | Pieniak et al. | 604/379 |
| 4,540,454 | 9/1985 | Pieniak et al | 156/62.2 |
| 4,573,988 | 3/1986 | Pieniak et al. | 604/379 |
| 4,578,070 | 3/1986 | Holtman | 604/378 |
| 4,596,567 | 6/1986 | Iskra | 604/368 |
| 4,673,402 | 9/1987 | Weisman et al. | 604/368 |
| 4,676,786 | 6/1987 | Nishino | 604/378 |
| 4,822,453 | 4/1989 | Dean et al. | 162/157.6 |
| 4,935,022 | 6/1990 | Lash et al. | 604/368 |
| 4,957,795 | 9/1990 | Riedel | 428/74 |
| 5,057,368 | 10/1991 | Largman et al. | 428/397 |
| 5,147,345 | 9/1992 | Young et al. | 604/378 |
| 5,164,045 | 11/1992 | Awofeso et al. | 162/101 |
| 5,167,764 | 12/1992 | Nielsen et al. | 162/146 |
| 5,167,765 | 12/1992 | Nielsen et al. | 162/146 |
| 5,204,165 | 4/1993 | Schortmann | 428/198 |
| 5,217,445 | 6/1993 | Young et al. | 604/381 |
| 5,231,122 | 7/1993 | Palumbo et al. | 524/30 |
| 5,334,176 | 8/1994 | Buenger et al. | 604/367 |
| 5,350,370 | 9/1994 | Jackson et al. | 604/367 |
| 5,360,420 | 11/1994 | Cook et al. | 604/378 |
| 5,391,161 | 2/1995 | Hellgren et al. | 604/366 |
| 5,397,435 | 3/1995 | Ostendorf et al | 162/112 |
| 5,405,501 | 4/1995 | Phan et al. | 162/127 |
| 5,409,572 | 4/1995 | Kershaw et al. | 162/109 |

FOREIGN PATENT DOCUMENTS

| | | |
|---|---|---|
| 0193309 | 9/1986 | European Pat. Off. . |
| 0391814 | 10/1990 | European Pat. Off. . |
| 0427316A2 | 5/1991 | European Pat. Off. . |
| 0427317A2 | 5/1991 | European Pat. Off. . |
| 0518291A1 | 12/1992 | European Pat. Off. . |
| 0518340A1 | 12/1992 | European Pat. Off. . |
| 0618239 | 10/1994 | European Pat. Off. . |
| 2269109 | 2/1994 | United Kingdom . |
| WO91/11162 | 8/1991 | WIPO . |
| WO94/21858 | 9/1994 | WIPO . |

*Primary Examiner*—David H. Willse
*Assistant Examiner*—Dennis Ruhl
*Attorney, Agent, or Firm*—William S. Andes; E. Kelly Linman; Jacobus C. Rasser

[57] ABSTRACT

The fluid distribution members according to the present invention preferably comprise three basic components: chemically stiffened, twisted, and curled bulking fibers, high surface area fibers, and thermoplastic binder fibers. Fluid distribution members according to the present invention use a high surface fiber to provide capillary pressure (or suction) to the fluid distribution member. These high surface area fibers are generally small and highly conformable. They provide the substrate with capillary pressure well in excess of the capillary pressure found in the bulk-providing chemically stiffened, twisted, and curled fibers alone. A presently preferred fiber for this high surface application is the eucalyptus family of wood pulp fibers. Eucalyptus provides the capillary pressure usually associated with cellulose fines, but at a large enough length and denier so as to not fill in the voids provided by the chemically stiffened, twisted, and curled fibers and will not easily pass through a forming screen.

20 Claims, 2 Drawing Sheets

FLUID DISTRIBUTION MEMBER FOR ABSORBENT ARTICLES EXHIBITING HIGH SUCTION AND HIGH CAPACITY

FIELD OF THE INVENTION

The present invention relates to fluid distribution members having improved fluid distribution and storage properties. The present invention further relates to absorbent structures incorporating such fluid distribution members which can be used in a variety of absorbent articles such as catamenial products, disposable diapers, adult incontinence pads and briefs, and the like.

BACKGROUND OF THE INVENTION

Absorbent webs which comprise entangled masses of fibers, i.e., fibrous webs, are well known in the art. Such webs can imbibe liquids, such as discharged body fluids, both by an absorption mechanism wherein fluid is taken up by the fiber material itself and by a wicking mechanism wherein fluid is acquired by, distributed through and stored in the capillary interstices between fibers. One means for improving the absorbent capacity of such fibrous web structures is to incorporate therein a superabsorbent material, such as polymeric gelling material (also referred to as hydrogel-forming material superabsorbent polymers, etc.) which imbibes fluid. The superabsorbent material serves to retain fluid such as discharged body liquids.

Notwithstanding the existence of absorbent cores as described above, there remains a need to provide absorbent cores with improved effective absorbent capacity. One way to theoretically do this would be to increase the level of polymeric gelling material in the absorbent core. Unfortunately, high levels of polymeric gelling material especially levels in excess of about 15%, in fibrous webs typically used in absorbent cores can induce a phenomena referred to as gel-blocking. Gel-blocking occurs when the polymeric gelling material located in regions first contacted with fluid increase in volume as a consequence of imbibing the fluid and forming the hydrogel. When polymeric gelling material concentration is too high, the hydrogel can block additional fluid from reaching other regions of the core having unused absorbent capacity. The occurrence of gel blocking can lead to leakage during usage of the absorbent article.

Polymeric gelling materials have been developed which can exhibit a reduced tendency to result in gel blocking. However, these improved polymeric gelling materials, and other superabsorbent materials, are subject to performance limitations of the web of cellulosic fibers in which particles of gelling material are distributed. In particular, upon initial wetting, the cellulosic fiber webs tend to collapse to a higher density and, consequently, exhibits reduced capacity, permeability, and fluid transport efficiency.

Another reason why many absorbent articles such as catamenial pads, adult incontinent products, and diapers are subject to leakage is inability to absorb second and subsequent discharges of fluid even if the first fluid discharge has been effectively absorbed. Leakage due to second and subsequent discharges is especially prevalent during the night, when users commonly experience multiple discharges before being attended to. One reason for the inability of many absorbent articles to adequately handle multiple discharges of fluid, in addition to the reasons discussed above, is the inability of the absorbent core to transport discharged fluid away from the region of discharge once the absorbent capacity of that region has been reached. Overall performance of the absorbent article is limited by the inability to have the fluid transported to the farthest reaches of the core.

One means which has been used to increase the fluid transport ability of the absorbent core is to create a smaller average pore regime by densification of a conventional core. While this does decrease the overall pore size average, generally the largest cells see the largest ratio of collapse and the smaller pores, which determine ultimate capillary pressure (vertical wicking height), see the least ratio of change. This loss of large pore capacity results in a high loss of capacity and more importantly, fluid permeability.

Another means which has been used in the past to increase the fluid transport ability of the absorbent core is to blend in certain amounts of fine fibers and particles which have a high surface area with chemically stiffened conventional cellulose fibers, non-stiffened cellulosic material, synthetic fibers, chemical additives and thermoplastic polymers. Since surface area per unit volume has a strong influence on the capillary pressure of a particular substrate, these high surface area fibers do provide higher vertical wicking. But the resulting structure tends to be very dense and has low fluid transport capability, or "flux", defined herein as the ability to move a certain amount of fluid through a given cross-section of a material to a particular height in a specific time. The increase in capillary pressure (height) from these fine fibers results in a more significant loss of volume transported to a given height.

SUMMARY OF THE INVENTION

The fluid distribution members according to the present invention preferably comprise three basic components: chemically stiffened, twisted, and curled bulking fibers, high surface area fibers, and thermoplastic binder fibers.

Fluid distribution members according to the present invention use a high surface fiber to provide capillary pressure (or suction) to the fluid distribution member. These high surface area fibers are generally small and highly conformable. They provide the substrate with capillary pressure well in excess of the capillary pressure found in the bulk-providing chemically stiffened, twisted, and curled fibers alone.

A presently preferred fiber for this high surface application is the eucalyptus family of wood pulp fibers. Eucalyptus provides the capillary pressure usually associated with cellulose fines, but at a large enough length and denier so as to not fill in the voids provided by the chemically stiffened, twisted, and curled fibers and will not easily pass through the forming screen. Particularly suitable eucalyptus fibers include those of the eucalyptus grandis species.

The fluid distribution members of the present invention can be advantageously utilized as a component of the absorbent core in various types of absorbent articles, e.g., disposable catamenial pads, diapers, and incontinence briefs, which also comprise a fluid pervious topsheet and a fluid impervious backsheet affixed to the topsheet, wherein the absorbent core is disposed therebetween.

BRIEF DESCRIPTION OF THE DRAWINGS

While the specification concludes with claims particularly pointing out and distinctly claiming the present invention, it is believed that the present invention will be better understood from the following description in conjunction with the accompanying Drawing Figures, in which like reference numerals identify like elements, and wherein:

DETAILED DESCRIPTION OF THE INVENTION

The fluid distribution members of the present invention can be utilized in disposable products which are capable of absorbing significant quantities of body fluids, such as urine, perspiration, menses, and water in body wastes. Such articles may be prepared in the form of disposable diapers, catemenial pads, adult incontinence briefs, tampons, and disposable towels and wipes, and the like.

The absorbent articles herein generally comprise three basic structural components. One such component is a substantially liquid impervious backsheet. On top of this backsheet is disposed an absorbent core which may itself comprise one or more distinct layers, and which may include a superabsorbent material in one or more of the layers. On top of this absorbent core and joined to the backsheet is a fluid pervious topsheet. The topsheet is the element of the article which is placed next to the skin of the wearer. As used herein, the term "joined" encompasses configurations whereby the topsheet is directly joined to the backsheet by affixing the topsheet directly to the backsheet around the perimeter of the absorbent core, and configurations whereby the topsheet is indirectly joined to the backsheet by affixing the topsheet to intermediate members which in turn are affixed to the backsheet. Preferably, the topsheet and backsheet are joined directly at the absorbent article's periphery by adhesive or other attachment means known in the art. The topsheet may also be adhered to the absorbent core.

A preferred disposable diaper or catemenial pad, for the purpose of this invention comprises an absorbent core; a topsheet superposed or co-extensive with one face of the core, and a liquid impervious backsheet superposed or co-extensive with the face of the core opposite the face covered by the topsheet. Both the backsheet and the topsheet most preferably have a width and length greater than that of the core thereby providing small marginal portions of the backsheet and topsheet which extend beyond the core. Frequently the backsheet and the topsheet will be fused together in these side marginal portions. The product is preferably constructed in a shaped configuration such as, but not limited to, an hourglass shape.

An absorbent core or absorbent structure according to the present invention comprises or includes a fluid distribution member as described hereinafter. It should be understood that for purposes of this invention that the term "layers" refers to identifiable components of the absorbent structure, and any structure referred to as a "layer" may actually comprise a laminate or combination of several sheets or webs of the requisite type of materials as hereinafter described. As used herein, the term "layer" includes the terms "layers" and "layered." For purposes of this invention, it should also be understood that the term "upper" refers to the layer of the absorbent core which is nearest to and faces the article topsheet; conversely, the term "lower" refers to the layer of the absorbent core which is nearest to and faces the article backsheet.

It should be noted that the various members, layers, and structures of absorbent articles according to the present invention may or may not be generally planar in nature, and may be shaped or profiled in any desired configuration.

Absorbent structures according to the present invention may include more than one layer or structure having the properties and characteristics attributed herein to the "fluid distribution member". Such absorbent structures may also include one or more layers having different compositional and functional characteristics, such as acquisition layers and storage layers, to provide functional attributes to augment those of the fluid distribution members of the present invention and enhance the overall performance of the absorbent structure.

Optionally, a fluid pervious sheet (e.g., a tissue sheet) or other scrim may be positioned between the fluid distribution member and another component to increase integrity of the fluid distribution member during processing and/or use. Such sheet or scrim can envelope all or part of the fluid distribution member only, or simply be positioned as described above without necessarily enveloping the fluid distribution member. Also, optionally, any layer or structure containing superabsorbent material can be enveloped with a fluid pervious sheet, such as a tissue paper sheet, to obviate user concerns with loose superabsorbent material.

Acquisition Layer

One element which is useful as a component of the absorbent structure hereof is an upper fluid acquisition layer which comprises a hydrophilic fibrous material, described more fully hereinafter. This fluid acquisition layer serves to quickly collect and temporarily hold discharged body fluid. A portion of discharged fluid may, depending upon the wearer's position, permeate the acquisition layer and be absorbed by the fluid distribution member in the area proximate to the discharge. However, since fluid is frequently discharged in gushes, the fluid distribution member in such area may not absorb the fluid as quickly as it is discharged. Therefore, the upper acquisition layer hereof also facilitates transport of the fluid from the point of initial fluid contact to other parts of the acquisition layer. In the context of the present invention, it should be noted that the term "fluid" includes, but is not limited to, liquids, urine, menses, perspiration, and water based body fluids.

The fluid function of the acquisition layer is of particular importance. The acquisition layer must have sufficient capillary suction to more fully drain the topsheet and yet not exhibit excessive fluid retention to make it difficult for the underlying layer (fluid distribution member) to desorb the acquisition layer.

The acquisition layer may be comprised of several different materials including nonwoven or woven webs of synthetic fibers including polyester, polypropylene, or polyethylene, natural fibers including cotton or cellulose, blends of such fibers, or any equivalent materials or combinations of materials.

Fluid Distribution Member

A. Composition of Fluid Distribution Member

The fluid distribution members according to the present invention preferably comprise three basic components: chemically stiffened, twisted, and curled bulking fibers, high surface area fibers, and binder fibers. Fluid distribution members preferably comprise from about 20% to about 80% of the chemically stiffened, twisted, and cured fibers, from about 10% to about 80% of a high surface area fiber, and from 0% to about 50% of a thermoplastic binding means for increasing physical integrity of the web. All percentages herein refer to weight percentages based on total dry web weight. Preferably, the fluid distribution members will comprise between about 45% and about 60% of chemically stiffened, twisted, and cured fibers, between about 5% and about 15% of a hot melt fibrous binding means, and between about 30% and about 45% high surface area cellulose binding means (hereafter described). More preferably, the fluid distribution members comprise about 10% thermoplastic binding means, about 45% chemically stiffened, twisted, and cured fibers, and about 45% high surface area fibers. Chemical additives can also be used as binding means, and are incorporated into the acquisition/distribution layer at levels typically of about 0.2% to about 2.0%, dry web weight basis. The three basic fiber components are described in greater detail below.

Chemically-stiffened/Twisted Bulking Fiber

The fluid distribution members of the present invention include chemically stiffened, twisted, and curled fibers as a majority constituent. As used herein, the term "chemically stiffened, twisted, and curled fibers" means any fibers which have been stiffened by chemical means to increase stiffness of the fibers under both dry and aqueous conditions. Such means include the addition of chemical stiffening agents which, for example, coat and/or impregnate the fibers. Such means also include the stiffening of the fibers by altering the chemical structure of the fibers themselves, e.g., by cross-linking polymer chains.

Fibers stiffened by crosslink bonds in individualized (i.e., fluffed) form are disclosed, for example, in Bernardin, U.S. Pat. No. 3,224,926, Issued Dec. 21, 1965; Chung, U.S. Pat. No. 3,440,135, Issued Apr. 22, 1969; Chatterjee, U.S. Pat. No. 3,932,209, Issued Jan. 13, 1976 and Sangenis et al., U.S. Pat. No. 4,035,147, Issued Jul. 12, 1977. More preferred fibers are disclosed in Dean et al., U.S. Pat. No. 4,822,453, issued Apr. 18, 1989, Dean et al., U.S. Pat. No. 4,888,093, issued Dec. 19, 1989, and Moore et al., U.S. Pat. No. 4,898,642, issued Feb. 6, 1990. All of these patents are incorporated herein by reference.

Without wishing to be bound by theory, in addition to being hydrophilic, these stiffened fibers are preferably substantially "hornified". Thus, the cell walls do not swell appreciably and maintain the void volume within the network. Chemically stiffened, twisted, and curled cellulosic fibers provide permeability, flexibility, and increased hydrophilicity. Since the fine fibers discussed herein are so small and highly conformable, chemically stiffened, twisted, and curled cellulosic fibers, with their stiffened twist/cuff, are one of the few materials which resist having interfiber voids filled with fine fibers. This ability to maintain an open capillary structure provides both loft and permeability, as well as void volume capacity.

For exemplary purposes, other polymeric stiffening agents which can coat or impregnate cellulosic fibers include: cationic modified starch having nitrogen-containing groups (e.g., amino groups) such as those available from National Starch and Chemical Corp., Bridgewater, N.J., USA; latex; wet strength resins such as polyamide-epichlorohydrin resin (e.g., Kymene™ 557H, Hercules, Inc. Wilmington, Del., USA), polyacrylamide resin (described, for example, in U.S. Pat. No. 3,556,932 issued Jan. 19, 1971 to Coscia, et al.; also, for example, the commercially available polyacrylamide marketed by American Cyanamid Co., Stanford, Conn., USA, under the trade name Parez™ 631 NC); urea formaldehyde and melamine formaldehyde resins, and polyethylenimine resins. A general dissertation on wet strength resins utilized in the paper art, and generally applicable herein, can be found in TAPPI monograph series No. 29. "Wet Strength in Paper and Paperboard", Technical Association of the Pulp and Paper Industry (New York, 1965).

The fibers utilized in the fluid distribution members herein are preferably stiffened by means of chemical reaction. For example crosslinking agents can be applied to the fibers which, subsequent to application, are caused to chemically form intra-fiber crosslink bonds. These crosslink bonds can increase stiffness of the fibers. Whereas the utilization of intrafiber crosslink bonds to chemically stiffen the fibers is preferred, it is not meant to exclude other types of reactions for chemical stiffening of the fibers.

In the more preferred stiffened fibers, chemical processing includes intrafiber crosslinking with crosslinking agents while such fibers are in a relatively dehydrated, defibrillated (i.e., individualized), twisted, curled condition. Suitable chemical stiffening agents include monomeric crosslinking agents including, but not limited to, $C_2$–$C_8$ dialdehydes and $C_2$–$C_8$ monoaldehydes having an acid functionality can be employed to form the crosslinking solution. These compounds are capable of reacting with at least two hydroxyl groups in a single cellulose chain or on approximately located cellulose chains in a single fiber. Such crosslinking agents contemplated for use in preparing the stiffened cellulose fibers include, but are not limited to, glutaraldehyde, glyoxal, formaldehyde, and glyoxylic acid. Other suitable stiffening agents are polycarboxylates, such as citric acid. The polycarboxylate stiffening agents and a process for making stiffened fibers from them are described in U.S. Pat. No. 5,190,563, issued Mar. 2, 1993, incorporated by reference herein. The effect of crosslinking under these conditions is to form fibers which are stiffened and which tend to retain their twisted, curled configuration during use in the absorbent articles herein. Such fibers, and processes for making them are described in the above incorporated patents.

Stiffened cellulose fibers herein having the preferred physical and performance characteristics herein before set forth, can be prepared by internally crosslinking such fibers in relatively dehydrated form while or after such fibers are being or have been dried and defibrated (i.e., "fluffed") as described in U.S. patent application Ser. No. 304,925, now U.S. Pat. No. 4,898,642. It is not, however, meant to necessarily exclude other hydrophilic, chemically stiffened, twisted, and curled fibers from this invention, such other fibers being described in (but, not limited to) the previously incorporated U.S. Pat. Nos. 3,224,926, 3,440,135, 4,035,147, and 3,932,209.

High Surface Area Fibers

Fluid distribution members according to the present invention use a high surface fiber to provide capillary pressure (or suction) to the fluid distribution member. These high surface area fibers are generally small and highly conformable. They provide the substrate with capillary pressure well in excess of the capillary pressure found in the bulk-providing chemically stiffened, twisted, and curled fibers alone.

A presently preferred fiber for this high surface application is the eucalyptus family of wood pulp fibers. Eucalyptus provides the capillary pressure usually associated with cellulose fines, but at a large enough length and denier so as to not fill in the voids provided by the chemically stiffened, twisted, and curled fibers and will not easily pass through the forming screen, as does a significant amount of the cellulose fines described below. Particularly suitable eucalyptus fibers include those of the eucalyptus grandis species.

Other suitable surface area generating fibers for addition to the stiffened cellulosic fibers prior to formation of the wet web from a pulp slurry include, but are not limited to, a variety of cellulosic and synthetic fibrous materials such as those disclosed in U.S. Pat. No. 5,217,445, issued to Young et al. on Jun. 8, 1993, herein incorporated by reference. Such materials include nonstiffened cellulosic fibers (i.e., conventional cellulosic pulp fibers), highly refined, nonstiffened, cellulosic fibers (preferably with Canadian Standard Freeness (CSF) of less than about 200 CSF, more preferably from about 40 CSF to about 100 CSF) referred to herein as "crill", and high surface area cellulosic material such as expanded cellulose fibers (hereinafter described). The high surface area cellulose is well mixed with the stiffened fibers in slurry and the slurry is wetlaid as described above. A blender, a deflaker, a valley beater, a refiner (e.g., single, cone, or double disk refiner), or other equipment known in the art, can be used to mix or declump the stiffened fibers and high surface area cellulose.

High surface area cellulose can also be made from cellulosic fibers by passing a liquid suspension of cellulose fibers through a small diameter orifice, in which the suspension is subjected to a pressure drop of at least 3000 psig and a high velocity shearing action, followed by a high velocity decelerating impact. Passage of the suspension through the orifice is repeated until a substantially stable suspension is obtained. See U.S. Pat. No. 4,483,743, Turbak et al., Nov. 20, 1984, incorporated herein by reference.

Hot Melt Adhesive Fiber Reinforcement

Relative to conventional non-stiffened cellulosic fibers, the crosslinked, twisted, stiffened fibers in combination with high surface area fibers described above form lower tensile strength sheets, particular in a wet condition. Therefore, in order to facilitate processing and provide product-specific mechanical properties, in both wet and dry states, a binding means is preferably integrally incorporated into or onto the web. This can be done by adding the binding means to pulp prior to web formation, by applying the binding means to a wetlaid web after deposition on a forming wire, and before drying, after drying, or a combination thereof.

Fluid distribution members according to the present invention alleviate these problems by the integration of a thermally bonded polymer micro web in the material. This micro-web is formed by the polymer bonding fibers (such as Hoechst-Celanese Copolyolefin Bicomponent fiber and the like . . . ) strongly bonding at fiber intersections. This polymer micro structure allows the web to survive the harsh softening processes. Therefore through tight control of the amount of out- of-plane extension of the web (ring roll (i.e., passing through corrugated rolls), creping, S-wrap, etc.), the thermally set polymer micro web properties significantly control and maintain the wet/dry tensile, flexibility, and resiliency, while permitting extensive mechanical softening while maintaining acceptable wet/dry tensile strength and resiliency.

In the preferred embodiment, the fluid distribution member comprises a wetlaid web of stiffened cellulosic fibers wherein the web is reinforced with between about 0% to about 50%, preferably between about 5% to about 25%, more preferably between about 7% to about 15%, of a thermoplastic binding material, wherein the thermoplastic binding material provides bond sites at intersections of the binding fibers with either other binding fibers, chemically stiffened, twisted, and curled cellulosic fibers, or high surface area fibers. Such thermally bonded webs can, in general, be made by forming a web comprising the stiffened cellulosic fibers and thermoplastic fibers, which are preferably evenly distributed throughout. The thermoplastic fibrous material can be intermixed with the stiffened cellulosic fibers and fine fibers in the aqueous slurry prior to web formation. Once formed, the web is thermally bonded by heating the web until the thermoplastic portion of the fibers melt. Specific non-limiting examples of suitable fibrous materials include polyester hot melt fibers (KODEL 410), bicomponent fibers, tricomponent fibers, mixtures thereof, and the like.

In addition, a crimped type polymer-based binder fiber will contribute added bulk to the web. A presently preferred polymer-based binder fiber of the crimped variety is Hoechst-Celanese Copolyolefin Bicomponent fiber, commerically available under the tradename CELBOND® from Hoechst Celanese Corporation, type 255, lot 33865A, having a detex of about 3.3, a denier of about 3.0, and a fiber length of about 6.4 mm.

The thermoplastic binding materials useful for the fluid distribution members herein include any hot melt adhesive which can be melted at temperatures which will not extensively damage the cellulosic fibers. Preferably, the melting point of the thermoplastic binding material will be less than about (175° C.), preferably between about 75° C. and about 175° C. In any case, the melting point should be no lower than temperatures at which the articles of this invention are likely to be stored, whereby melting point will be typically no lower than about 50° C.

The thermoplastic binding material may, for example, be polyethylene, polypropylene, polyester, polyvinyl chloride, polyvinylidene chloride.

Preferably, the thermoplastic fibers will not significantly imbibe or absorb aqueous fluid. However, the surface of the thermoplastic material can be hydrophilic or hydrophobic. (As used herein, the terms "hydrophilic" and "hydrophobic" shall refer to the extent to which the surfaces are wetted by water.) Hydrophilic material becomes more preferred at higher thermoplastic levels, particularly at levels above about 40%.

Thermoplastic fibers for use herein can be on the order of about 0.1 cm to about 6 cm long, preferably from about 0.3 cm to about 3.0 cm.

The thermoplastic is preferably melted by through-air bonding, however other methods such as infra red light, steam drum drying, Yankee, etc. are not meant to be excluded. In another variation, the web is subjected to heat embossing on one or both faces of the web. This technique is described in further detail in U.S. Pat. No. 4,590,114, which was previously incorporated into this specification.

As discussed previously, scrims such as tissue sheets and other water pervious nonwoven sheets can be used as external support in addition to or in place of the binding means described above.

Other binding means for increasing physical integrity of the distribution layer and/or facilitating processing of webs, especially wetlaid webs, for use as the distribution layer include, chemical additives, such as resinous binders, latex, and starch known in the art for providing increased integrity to fibrous webs. Suitable resinous binders include those which are known for their ability to provide wet strength in paper structures, such as can be found in TAPPI monograph series No. 29, Wet Strength in Paper and Paperboard, Technical Association of the Pulp and Paper Industry (New York, 1965), incorporated herein by reference. Suitable resins include polyamide-epichlorohydrin and polyacrylamide resins. Other resins finding utility in this invention are urea formaldehyde and melamine formaldehyde resins. The more common functional groups of these polyfunctional resins are nitrogen containing groups such as amino groups and methylol groups attached to nitrogen. Polyethylenimine type resins may also find utility in the present invention.

Starch, particularly cationic, modified starches may also find utility as chemical additives in the present invention. Such cationic starch materials, generally modified with nitrogen containing groups such as amino groups and methylol groups attached to nitrogen, may be obtained from Natural Starch and Chemical Corporation, located in Bridgewater, N.J. Other suitable binders include, but are not limited to, polyacrylic acid, polyvinyl alcohol, polyvinyl acetate.

The level of chemical additive binders which are added will typically be from about 0.25% to about 2% total web weight basis. Chemical additive binders which are hydrophilic, however, can be utilized in larger quantities. If the chemical binder additives are added to the stiffened fibers in aqueous slurry, conventional, nonstiffened cellulosic fibers or high surface area cellulose is preferably also present, to enhance retention of the chemical additive binder. Chemical additive binders can be applied to dried or undried webs by printing, spraying, or other methods known in the art.

Material Formation Process

The constituent components of the fluid distribution members of the present invention may be blended together and formed into webs by a variety of methods, including wet-laying methods, air-laying methods, carding, and other methods, of which wet-laying methods are presently preferred.

Techniques for wetlaying cellulosic fibrous material to form sheets such as dry lap and paper are well known in the art. These techniques are generally applicable to the wet-laying of the stiffened fibers to form wetlaid sheets useful in the absorbent structures of this invention. Suitable wetlaying techniques include handsheeting, and wetlaying with the utilization of paper making machines as disclosed, for instance, by L. H. Sanford et at. in U.S. Pat. No. 3,301,746. Due to the behavior of chemically stiffened, twisted, and cured fibers, particularly their tendency to flocculate in aqueous slurries, certain processing modifications, hereafter described, are preferably implemented when wetlaying with paper making machines.

In general, wetlaid webs can be made by depositing an aqueous slurry of fibers on to a foraminous forming wire, dewatering the wetlaid slurry to form a wet web, and drying the wet web. Preferably, the aqueous slurries of fibers for wetlaying will have a fiber consistency of between about 0.02% and about 2.0%, preferably between about 0.02% and about 0.2%, total slurry weight basis. Deposition of the slurry is typically accomplished using an apparatus known in the art as a headbox. The headbox has an opening, known as a slice, for delivering the aqueous slurry of fibers onto the foraminous forming wire. The forming wire can be of construction and mesh size used for dry lap or other paper making processing. Preferably, mesh sizes of about 70 to about 100 (Tyler standard screen scale) are used. (All mesh sizes referred to herein shall be based upon the Tyler standard screen scale, unless otherwise specifically indicated.) Conventional designs of headboxes known in the art for drylap and tissue sheet formation may be used. Suitable commercially available headboxes include, for example, open, fixed roof, twin wire, inclined wire, and drum former headboxes.

Once formed, the wet web is dewatered and dried. Dewatering can be performed with suction boxes or other vacuum devices. Typically, dewatering increases the fiber consistency to between about 8% and about 30%, total wet web weight basis, preferably between about 8% and about 23%. Dewatering to consistencies above about 23% may require wet-pressing and is less preferred. After dewatering, the web can be, but is not necessarily, transferred from the forming wire to a drying fabric which transports the web to drying apparatuses.

Drying of the wet web may be accomplished utilizing many techniques known in the art. It is particularly important that the web be dried thoroughly and uniformly at a temperature which fuses the thermoplastic binding material to other fibrous materials, but not so high as to cause the thermoplastic binding material to flow into the void volume of the network. Drying can be accomplished via, for example, a thermal blow-through dryer, a thermal air-impingement dryer, and heated drum dryers, including Yankee dryers. The wetlaid webs are preferably dried to completion (generally to fiber consistencies between about 95% to about 98%). The flexibility of the fully dried web is preferably increased. Suitable methods of increasing web flexibility would include creping the web using a Yankee dryer with a doctor blade, or using one of several mechanical techniques such as creping or microcreping using doctor blades or opposed rolls, s-wrapping, rolling with corrugated rolls, or other techniques well known in the art. The process of increasing the flexibility or softness of the web may be accomplished as part of the web formation process or as a separate post-formation operation.

In addition to preferred wetlaying processes of the types described above, under some circumstances it may be desirable to form fluid distribution members according to the present invention by airlaying, carding, or other suitable methods.

Storage Layer

Absorbent structures according to the present invention may optionally include additional layer(s) having primarily fluid storage characteristics. Such storage layers typically have limited transport and wicking capabilities but high storage or retention capacity, and rely upon the fluid distribution member to distribute incoming fluid over a larger area.

Storage layers or members may be of generally conventional design and composition, selected with regard to the particular application. The storage layer or member may be monolayer or multilayer, homogeneous or stratified, profiled or uniform, etc. Materials suitable for use in such storage members may be natural or synthetic in origin, woven, non-woven, fibrous, cellular, or particulate, and may include particles, layers, or regions of absorbent polymeric gelling materials. Storage members may also have any desired size and/or shape as may prove suitable for a particular application, including square, rectangular, oval, elliptical, oblong, etc. They may also take on a three-dimensional shape or may be substantially planar in nature.

Illustrative Absorbent Articles

As used herein, the term "absorbent article" refers to devices which absorb and contain body exudates, and, more specifically, refers to devices which are placed against or in proximity to the body of the wearer to absorb and contain the various exudates discharged from the body. The term "disposable" is used herein to describe absorbent articles which are not intended to be laundered or otherwise restored or reused as an absorbent article (i.e., they are intended to be discarded after a single use, and, preferably, to be recycled, composted or otherwise disposed of in an environmentally compatible manner). A "unitary" absorbent article refers to absorbent articles which are formed of separate parts united together to form a coordinated entity so that they do not require separate manipulative parts like a separate holder and pad.

Figure 1:
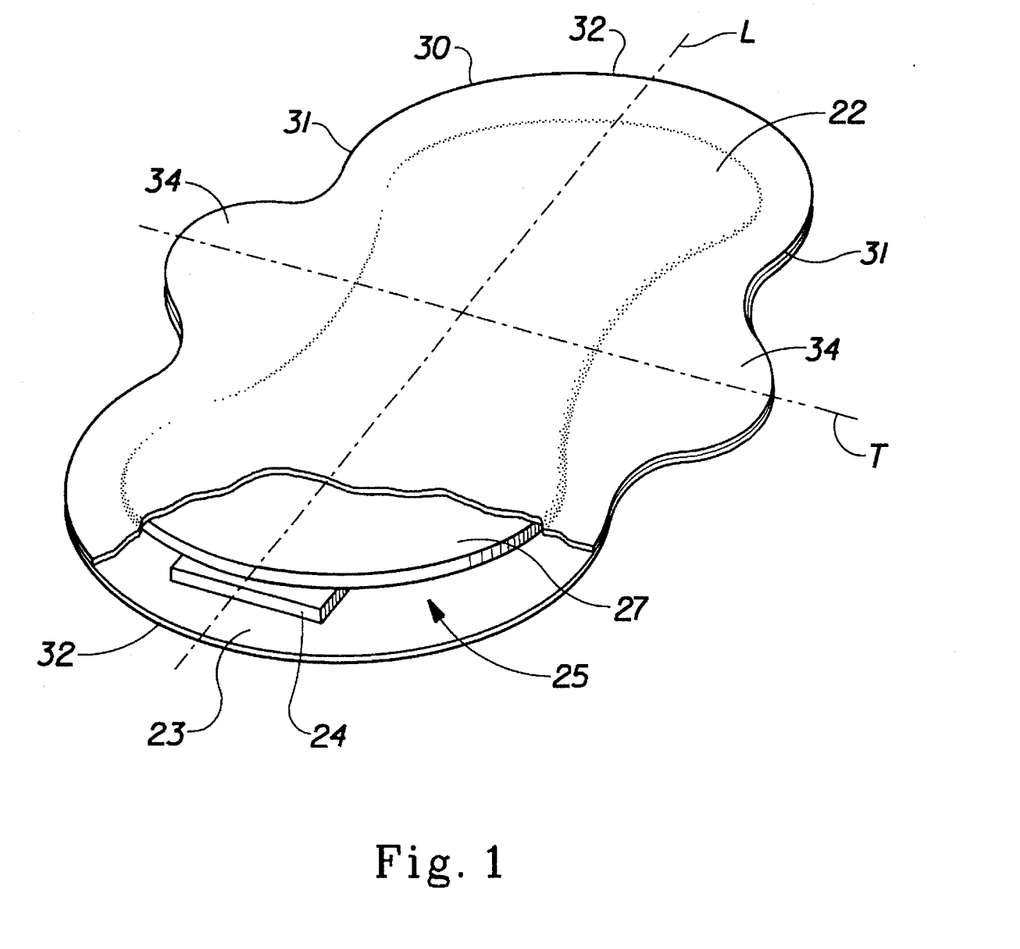
FIG. 1 is a perspective view, partially sectioned, of a preferred embodiment of an absorbent article in the form of a catemenial product which includes a fluid distribution member according to the present invention.

A preferred embodiment of a unitary disposable absorbent article of the present invention is the catamenial pad, sanitary napkin 20, shown in FIG. 1. As used herein, the term "sanitary napkin" refers to an absorbent article which is worn by females adjacent to the pudendal region, generally external to the urogenital region, and which is intended to absorb and contain menstrual fluids and other vaginal discharges from the wearer's body (e.g., blood, menses, and urine). Interlabial devices which reside partially within and partially external of the wearer's vestibule are also within the scope of this invention. As used herein, the term "pudendal" refers to the externally visible female genitalia. It should be understood, however, that the present invention is also applicable to other feminine hygiene or catamenial pads such as pantiliners, or other absorbent articles such as incontinence pads, tampons, and the like.

FIG. 1 is a plan view of the sanitary napkin 20 of the present invention in its flat-out state with portions of the structure being cut-away to more clearly show the construction of the sanitary napkin 20. The portion of the sanitary napkin 20 which faces or contacts the wearer is oriented towards the viewer. As shown in FIG. 1, the sanitary napkin 20 preferably comprises a liquid pervious topsheet 22, a liquid impervious backsheet 23 joined with the topsheet 22, and an absorbent core 25 positioned between the topsheet 22 and the backsheet 23. The sanitary napkin 20 depicted in FIG. 1 is a simplified absorbent article that could represent a sanitary napkin prior to its being placed on a wearer's undergarment. It should be understood, however, that the present invention is not limited to the particular type or configuration of sanitary napkin shown in FIG. 1.

The sanitary napkin 20 has two surfaces, a body-contacting surface or "body surface" and a garment surface. The sanitary napkin 20 is shown in FIG. 1 as viewed from its body surface. The body surface is intended to be worn adjacent to the body of the wearer while the garment surface is on the opposite side and is intended to be placed adjacent to the wearer's undergarments when the sanitary napkin 20 is worn. The sanitary napkin 20 has two centerlines, a longitudinal centerline "L" and a transverse centerline "T". The term "longitudinal", as used herein, refers to a line, axis or direction in the plane of the sanitary napkin 20 that is generally aligned with (e.g., approximately parallel to) a vertical plane which bisects a standing wearer into left and right body halves when the sanitary napkin 20 is worn. The terms "transverse" or "lateral" as used herein, are interchangeable, and refer to a line, axis or direction which lies within the plane of the sanitary napkin 20 that is generally perpendicular to the longitudinal direction. FIG. 1 also shows that the sanitary napkin 20 has a periphery 30 which is defined by the outer edges of the sanitary napkin 20 in which the longitudinal edges (or "side edges") are designated 31 and the end edges (or "ends") are designated 32. In the embodiment depicted in FIG. 1, the sanitary napkin 20 is symmetrical with respect to both the longitudinal and transverse centerlines.

Sanitary napkin 20 preferably includes side flaps or "wings" 34 that are folded around the crotch portion of the wearer's panties. The side flaps 34 can serve a number of purposes, including, but not limited to, protecting the wearer's panties from soiling and keeping the sanitary napkin secured to the wearer's panties.

While the topsheet, the backsheet, and the absorbent core may be assembled in a variety of well known configurations (including so called "tube" products or side flap products), preferred sanitary napkin configurations are described generally in U.S. Pat. No. 4,950,264, "Thin, Flexible Sanitary Napkin" issued to Osborn on Aug. 21, 1990; U.S. Pat. No. 4,425,130, "Compound Sanitary Napkin" issued to DesMarais on Jan. 10, 1984; U.S. Pat. No. 4,321,924, "Bordered Disposable Absorbent Article" issued to Ahr on Mar. 30, 1982; U.S. Pat. No. 4,589,876, "Shaped Sanitary Napkin With Flaps" issued to Van Tilburg on Aug. 18, 1987. Each of these patents are hereby incorporated herein by reference. FIG. 1 shows a preferred embodiment of the sanitary napkin 20 in which the topsheet 22 and the backsheet 23 have length and width dimensions generally larger than those of the absorbent core 25. The topsheet 22 and the backsheet 23 extend beyond the edges of the absorbent core 25 to thereby form not only portions of the periphery but also side flaps.

As best seen from FIG. 1, the backsheet 23 and the topsheet 22 are positioned adjacent the garment surface and the body surface, respectively, of sanitary napkin 20 and are preferably joined to each other to form a perimeter 30. For example, the backsheet 23 and the topsheet 22 can be secured to each other by a uniform continuous layer of adhesive, a patterned layer of adhesive, or an array of separate lines, spirals, or spots of adhesive. Adhesives that have been found to be satisfactory are manufactured by H. B. Fuller Company of St. Paul, Minn. under the designation HL-1258 or H-2031. Alternatively, topsheet 22 and backsheet 23 can be joined to each other by heat bonding, pressure bonding, ultrasonic bonding, dynamic mechanical bonding, or any other suitable method for joining topsheets and backsheets known in the art. A particularly suitable method for joining topsheet 22 and backsheet 23 together is by a crimp seal.

A fluid impermeable seal is provided in the border segment along perimeter 30. This seal is adapted to prevent lateral migration (i.e., "wicking") of fluid from perimeter 30 of sanitary napkin 20 through the peripheral edges 31 and 32, thereby inhibiting premature side soiling of the wearer's undergarments. As a result, topsheet 22 and backsheet 23 tend to remain relatively free of fluids. The seal is preferably disposed laterally inwardly as close as possible to perimeter 30 so that a greater portion of the border segment remains dry and unsoiled. The seal preferably completely surrounds perimeter 30 without any gaps that would allow wicking and fluid leakage.

The seal is preferably formed by the simultaneous application of pressure, with or without heat, commonly referred to as a "crimping" operation. During the "crimping" process, sufficient pressure, optionally with heat, is applied to melt topsheet 22 and backsheet 23, thereby forming the seal. Portions of the border region outside of the seal are crimped with discrete spaced-apart bonds. This discrete bonding creates a reverse or negative capillary gradient so that any fluids inadvertently passing through the seal will tend to be attracted toward the more dense material in the area of the seal; any fluid movement outside the seal occurs along the seal, as opposed to toward the outer edge of the border.

The absorbent core 25 according to the present invention comprises the improved distribution member 24 described above, which may be manufactured in a wide variety of sizes and shapes (e.g., rectangular, oval, hourglass, dog bone, asymmetric, etc.). The configuration and construction of the absorbent core may also be varied (e.g., the absorbent core may have varying caliper zones (e.g., profiled so as to be thicker in the center), hydrophilic gradients, superabsorbent gradients, or lower density and lower average basis weight acquisition zones; or may comprise one or more layers or structures). The total absorbent capacity of the absorbent core should, however, be compatible with the design loading and the intended use of the sanitary napkin. Further, the size and absorbent capacity of the absorbent core may be varied to accommodate different uses such as incontinence pads, pantiliners, regular sanitary napkins, or overnight sanitary napkins.

The fluid distribution member 24 according to the present invention may comprise a single, unitary, homogeneous layer or strata of the herein-described material. Alternatively, the fluid distribution member 24 may comprise two or more layers of such material either superimposed or formed into a cohesive laminate structure. Intervening layers of other materials, in particulate, web, or fiber form may be disposed between such layers.

Multiple layers of the materials of the present invention may also be employed having differing compositions or proportions of one or more constituent components. By way of illustrating but one of the many possible configurations, a fluid distribution member 24 may comprise a three layer laminate structure comprising upper and lower sub-layers having a composition of about 45% chemically stiffened, twisted, and curled fibers, about 45% eucalyptus fibers, and about 10% bicomponent fibers, between which a sub-layer of particulate absorbent gelling material has been incorporated. Layers or sub-layers of fluid distribution members according to the present invention may also have comparable or differing basis weights and/or densities.

In the preferred embodiment depicted in FIG. 1, the absorbent core 25 of sanitary napkin 20 also preferably includes an optional secondary topsheet or acquisition layer 27 between the distribution member 24 and the topsheet 22.

If desired, additional absorbent structures such as storage members may be incorporated into the sanitary napkin 20, and may be formed from a wide variety of liquid-absorbent materials commonly used in sanitary napkins and other absorbent articles such as comminuted wood pulp which is generally referred to as airfelt. Examples of other suitable absorbent materials include creped cellulose wadding; melt-blown polymers including coform; chemically stiffened, modified or cross-linked cellulosic fibers; synthetic fibers such as crimped polyester fibers; peat moss; tissue including tissue wraps and tissue laminates; absorbent foams; absorbent sponges; superabsorbent polymers; absorbent gelling materials; or any equivalent material or combinations of materials, or mixtures of these. Such additional layers may be included above or below the fluid distribution member 25, and/or in between the fluid distribution member 25 and another component such as acquisition layer 27.

Exemplary absorbent structures for use as the absorbent core of the present invention are described in U.S. Pat. No. 4,950,264 entitled "Thin, Flexible Sanitary Napkin" issued to Osborn on Aug. 21, 1990; U.S. Pat. No. 4,610,678 entitled "High-Density Absorbent Structures" issued to Weisman et al. on Sep. 9, 1986; U.S. Pat. No. 4,834,735 entitled "High Density Absorbent Members Having Lower Density and Lower Basis Weight Acquisition Zones", issued to Alemany et al. on May 30, 1989; and European Patent Application No. 0 198 683, The Procter & Gamble Company, published Oct. 22, 1986 in the name of Duenk, et al. Each of these patents are incorporated herein by reference.

In a preferred embodiment of the present invention, an acquisition layer(s) 27 may be positioned between the topsheet 22 and the distribution member 25. The acquisition layer serves to quickly collect and temporarily hold discharged bodily fluids, as well as facilitating transport the fluid from the point of initial fluid contact to other parts of the acquisition layer and the absorbent core. There are several reasons why the improved transport of exudates is important, including providing a more even distribution of the exudates throughout the absorbent core and allowing the sanitary napkin 20 to be made relatively thin. The transport referred to herein may encompass the transportation of liquids in one, two or all directions (i.e., in the x-y plane and/or in the z-direction).

The acquisition layer may be comprised of several different materials including nonwoven or woven webs of synthetic fibers including polyester, polypropylene, or polyethylene, natural fibers including cotton or cellulose, blends of such fibers, or any equivalent materials or combinations of materials. Examples of sanitary napkins having an acquisition layer and a topsheet are more fully described in U.S. Pat. No. 4,950,264 issued to Osborn and U.S. patent application Ser. No. 07/810,774, "Absorbent Article Having Fused Layers", filed Dec. 17, 1991 in the names of Cree, et al. Each of these references are incorporated herein by reference. In a preferred embodiment, the acquisition layer may be joined with the topsheet by any of the conventional means for joining webs together, most preferably by fusion bonds as is more fully described in the above-referenced Cree application.

The backsheet 23 is impervious to liquids (e.g., menses and/or urine) and is preferably manufactured from a thin plastic film, although other flexible liquid impervious materials may also be used. As used herein, the term "flexible" refers to materials which are compliant and will readily conform to the general shape and contours of the human body. The backsheet 23 prevents the exudates absorbed and contained in the absorbent core 25 from wetting articles which contact the sanitary napkin 20 such as pants, pajamas and undergarments. The backsheet 23 may thus comprise a woven or nonwoven material, polymeric films such as thermoplastic films of polyethylene or polypropylene, or composite materials such as a film-coated nonwoven material. Preferably, the backsheet is a polyethylene film having a thickness of from about 0.012 mm (0.5 mil) to about 0.051 mm (2.0 mils). Exemplary polyethylene films are manufactured by Clopay Corporation of Cincinnati, Ohio, under the designation P18-0401 and by Ethyl Corporation, Visqueen Division, of Terre Haute, Ind., under the designation XP-39385. The backsheet is preferably embossed and/or matte finished to provide a more clothlike appearance. Further, the backsheet 23 may permit vapors to escape from the absorbent core 24 (i.e., breathable) while still preventing exudates from passing through the backsheet 23.

The topsheet 22 is compliant, soft feeling, and non-irritating to the wearer's skin. Further, the topsheet 22 is liquid pervious permitting liquids (e.g., menses and/or urine) to readily penetrate through its thickness. A suitable topsheet 22 may be manufactured from a wide range of materials such as woven and nonwoven materials; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers.

Preferred topsheets for use in the present are selected from high loft nonwoven topsheets and aperture formed film topsheets. Apertured formed films are especially preferred for the topsheet because they are pervious to body exudates and yet non-absorbent and have a reduced tendency to allow fluids to pass back through and rewet the wearer's skin. Thus, the surface of the formed film which is in contact with the body remains dry, thereby reducing body soiling and creating a more comfortable feel for the wearer. Suitable formed films are described in U.S. Pat. No. 3,929,135, entitled "Absorptive Structures Having Tapered Capillaries", which issued to Thompson on Dec. 30, 1975; U.S. Pat. No. 4,324,246 entitled "Disposable Absorbent Article Having A Stain Resistant Topsheet", which issued to Mullane, et al. on Apr. 13, 1982; U.S. Pat. No. 4,342,314 entitled "Resilient Plastic Web Exhibiting Fiber-Like Properties", which issued to Radel. et al. on Aug. 3, 1982; U.S. Pat. No. 4,463,045 entitled "Macroscopically Expanded Three-Dimensional Plastic Web Exhibiting Non-Glossy Visible Surface and Cloth-Like Tactile Impression", which issued to Ahr et al. on Jul. 31, 1984; and U.S. Pat. No. 5,006,394 "Multilayer Polymeric Film" issued to Baird on Apr. 9, 1991. Each of these patents are incorporated herein by reference. The preferred topsheet for the present invention is the formed film described in one or more of the above patents and marketed on sanitary napkins by The Procter & Gamble Company of Cincinnati, Ohio as "DRI-WEAVE".

In a preferred embodiment of the present invention, the body surface of the formed film topsheet is hydrophilic so as to help liquid to transfer through the topsheet faster than if the body surface was not hydrophilic so as to diminish the likelihood that menstrual fluid will flow off the topsheet rather than flowing into and being absorbed by the absorbent core. In a preferred embodiment, surfactant is incorporated into the polymeric materials of the formed film topsheet such as is described in U.S. patent application Ser. No. 07/794,745, "Absorbent Article Having A Nonwoven and Apertured Film Coversheet" filed on Nov. 19, 1991 by Aziz, et al., which is incorporated herein by reference. Alternatively, the body surface of the topsheet can be made hydrophilic by treating it with a surfactant such as is described in the above referenced U.S. Pat. No. 4,950,254 issued to Osborn, incorporated herein by reference.

In use, the sanitary napkin 20 can be held in place by any support means or attachment means (not shown) well-known for such purposes. Preferably, the sanitary napkin is placed in the user's undergarment or panty and secured thereto by a fastener such as an adhesive. The adhesive provides a means for securing the sanitary napkin in the crotch portion of the panty. Thus, a portion or all of the outer surface of the backsheet 23 is coated with adhesive. Any adhesive or glue used in the art for such purposes can be used for the adhesive herein, with pressure-sensitive adhesives being preferred. Suitable adhesives are Century A-305-IV manufactured by the Century Adhesives Corporation of Columbus, Ohio; and Instant Lock 34-2823 manufactured by the National Starch and Chemical Company of Bridgewater, N.J. Suitable adhesive fasteners are also described in U.S. Pat. No. 4,917,697.

Before the sanitary napkin is placed in use, the pressure-sensitive adhesive is typically covered with a removable release liner in order to keep the adhesive from drying out or adhering to a surface other than the crotch portion of the panty prior to use. Suitable release liners are also described in the above-referenced U.S. Pat. No. 4,917,697. Any commercially available release liners commonly used for such purposes can be utilized herein. Non-limiting examples of suitable release liners are BL30MG-A Silox E1/0 and BL30MG-A Silox 4P/O both of which are manufactured by the Akrosil Corporation of Menasha, Wis. The sanitary napkin 20 of the present invention is used by removing the release liner and thereafter placing the sanitary napkin in a panty so that the adhesive contacts the panty. The adhesive maintains the sanitary napkin in its position within the panty during use.

Figure 2:
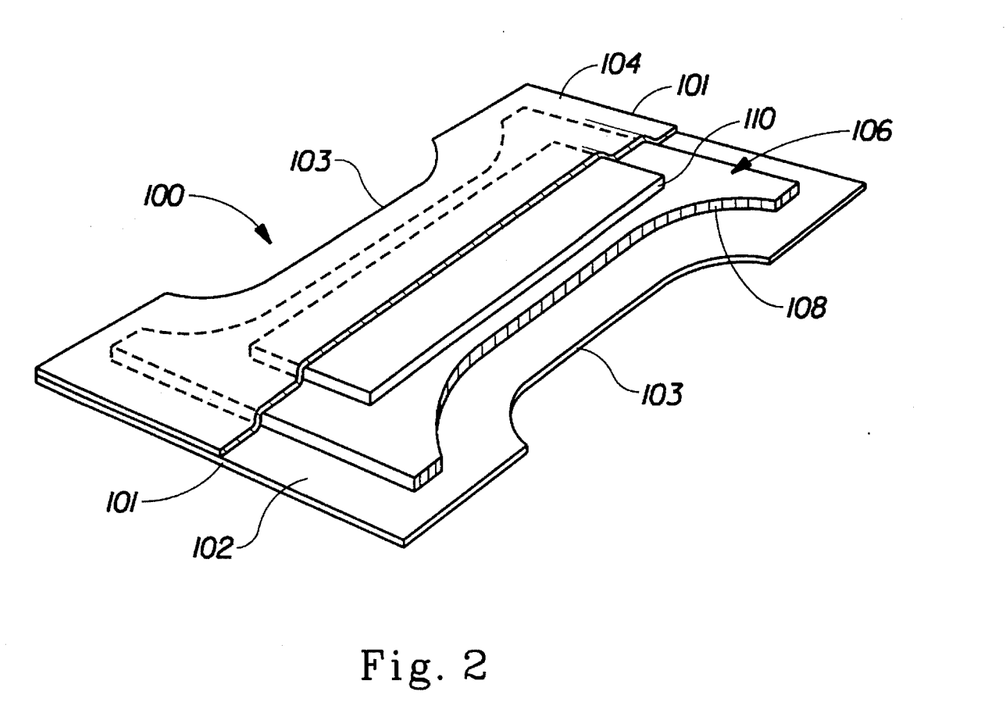
FIG. 2 is a perspective view, partially sectioned, of a preferred embodiment of an absorbent article in the form of a diaper which includes a fluid distribution member according to the present invention.

A preferred embodiment of a disposable absorbent article in the form of a diaper 100, is shown in FIG. 2. As used herein, the term "diaper" refers to a garment generally worn by infants and incontinent persons that is worn about the lower torso of the wearer. It should be understood, however, that the present invention is also applicable to other absorbent articles such as incontinent briefs, incontinent pads, training pants, diaper inserts, sanitary napkins, facial tissues, paper towels, and the like. The diaper 100 depicted in FIG. 2 is a simplified absorbent article that could represent a diaper prior to its being placed on a wearer. It should be understood, however, that the present invention is not limited to the particular type or configuration of diaper shown in FIG. 2.

FIG. 2 is a perspective view of the diaper 100 of the present invention in its uncontracted state (i.e., with all the elastic induced contraction removed) with portions of the structure being cut-away to more deafly show the construction of the diaper 100. The portion of the diaper 100 which contacts the wearer faces the viewer. The diaper 100 is shown in FIG. 2 to preferably comprise a liquid pervious topsheet 104; a liquid impervious backsheet 102 joined with the topsheet 104; and an absorbent core 106 positioned between the topsheet 104 and the backsheet 102. Additional structural features such as elastic members and fastening means for securing the diaper in place upon a wearer (such as tape tab fasteners) may also be included.

While the topsheet 104, the backsheet 102, and the absorbent core 106 can be assembled in a variety of well known configurations, a preferred diaper configuration is described generally in U.S. Pat. No. 3,860,003 (Buell), issued Jan. 14, 1975, which is incorporated by reference. Alternatively preferred configurations for disposable diapers herein are also disclosed in U.S. Pat. No. 4,808,178 (Aziz et al), issued Feb. 28, 1989; U.S. Pat. No. 4,695,278 (Lawson), issued Sep. 22, 1987; and U.S. Pat. No. 4,816,025 (Foreman), issued Mar. 28, 1989, all of which are incorporated by reference.

FIG. 2 shows a preferred embodiment of the diaper 100 in which the topsheet 104 and the backsheet 102 are co-extensive and have length and width dimensions generally larger than those of the absorbent core 106. The topsheet 104 is joined with and superimposed on the backsheet 102 thereby forming the periphery of the diaper 100. The periphery defines the outer perimeter or the edges of the diaper 100. The periphery comprises the end edges 101 and the longitudinal edges 103.

The topsheet 104 is compliant, soft feeling, and non-irritating to the wearer's skin. Further, the topsheet 104 is liquid pervious permitting liquids to readily penetrate through its thickness. A suitable topsheet 104 can be manufactured from a wide range of materials such as porous foams, reticulated foams, apertured plastic films, natural fibers (e.g., wood or cotton fibers), synthetic fibers (e.g., polyester or polypropylene fibers) or from a combination of natural and synthetic fibers. Preferably, the topsheet 104 is made of a hydrophobic material to isolate the wearer's skin from liquids in the absorbent core 106.

A particularly preferred topsheet 104 comprises staple length polypropylene fibers having a denier of about 1.5, such as Hercules type 151 polypropylene marketed by Hercules, Inc. of Wilmington, Del. As used herein, the term "staple length fibers" refers to those fibers having a length of at least about 15.9 mm (0.62 inches).

There are a number of manufacturing techniques which can be used to manufacture the topsheet 104. For example, the topsheet 104 can be woven, nonwoven, spunbonded, carded, or the like. A preferred topsheet is carded, and thermally bonded by means well known to those skilled in the fabrics art. Preferably, the topsheet 104 has a weight from about 18 to about 25 grams per square meter, a minimum dry tensile strength of at least about 400 grams per centimeter in the machine direction, and a wet tensile strength of at least about 55 grams per centimeter in the cross-machine direction.

The backsheet 102 is impervious to liquids and is preferably manufactured from a thin plastic film, although other flexible liquid impervious materials may also be used. The backsheet 102 prevents the exudates absorbed and contained in the absorbent core 106 from wetting articles which contact the diaper 100 such as bed sheets and undergarments. Preferably, the backsheet 102 is polyethylene film having a thickness from about 0.012 mm (0.5 rail) to about 0.051 centimeters (2.0 mils), although other flexible, liquid impervious materials can be used. As used herein, the term "flexible" refers to materials which are compliant and which will readily conform to the general shape and contours of the wearer's body.

A suitable polyethylene film is manufactured by Monsanto Chemical Corporation and marketed in the trade as Film No. 8020. The backsheet 102 is preferably embossed and/or matte finished to provide a more clothlike appearance. Further, the backsheet 102 may permit vapors to escape from the absorbent core 106 while still preventing exudates from passing through the backsheet 102.

The size of the backsheet 102 is dictated by the size of the absorbent core 106 and the exact diaper design selected. In a preferred embodiment, the backsheet 102 has a modified hourglass-shape extending beyond the absorbent core 106 a minimum distance of at least about 1.3 centimeters to about 2.5 centimeters (about 0.5 to about 1.0 inch) around the entire diaper periphery.

The topsheet 104 and the backsheet 102 are joined together in any suitable manner. As used herein, the term "joined" encompasses configurations whereby the topsheet 104 is directly joined to the backsheet 102 by affixing the topsheet 104 directly to the backsheet 102, and configurations whereby the topsheet 104 is indirectly joined to the backsheet 102 by affixing the topsheet 104 to intermediate members which in turn are affixed to the backsheet 102. In a preferred embodiment, the topsheet 104 and the backsheet 102 are affixed directly to each other in the diaper periphery by attachment means (not shown) such as an adhesive or any other attachment means as known in the art. For example, a uniform continuous layer of adhesive, a patterned layer of adhesive, or an array of separate lines or spots of adhesive can be used to affix the topsheet 104 to the backsheet 102.

Tape tab fasteners (not shown for clarity) are typically applied to the back waistband region of the diaper 102 to provide a fastening means for holding the diaper on the wearer. The tape tab fasteners can be any of those well known in the art, such as the fastening tape disclosed in U.S. Pat. No. 3,848,594 (Buell), issued Nov. 19, 1974, which is incorporated by reference. These tape tab fasteners or other diaper fastening means are typically applied near the corners of the diaper 100.

Elastic members (also not shown for clarity) are disposed adjacent the periphery of the diaper 100, preferably along each longitudinal edge 103, so that the elastic members tend to draw and hold the diaper 100 against the legs of the wearer. Alternatively, the elastic members can be disposed adjacent either or both of the end edges 101 of the diaper 100 to provide a waistband as well as or rather than leg cuffs. For example, a suitable waistband is disclosed in U.S. Pat. No. 4,515,595 (Kievit et al), issued May 7, 1985, which is incorporated by reference. In addition, a method and apparatus suitable for manufacturing a disposable diaper having elastically contractible elastic members is described in U.S. Patent 4,081,301 (Buell), issued Mar. 28, 1978, which is incorporated by reference.

The elastic members are secured to the diaper 100 in an elastically contractible condition so that in a normally unrestrained configuration, the elastic members effectively contract or gather the diaper 100. The elastic members can be secured in an elastically contractible condition in at least two ways. For example, the elastic members can be stretched and secured while the diaper 100 is in an uncontracted condition. Alternatively, the diaper 100 can be contracted, for example, by pleating, and the elastic members secured and connected to the diaper 100 while the elastic members are in their unrelaxed or unstretched condition. The elastic members may extend along a portion of the length of the diaper 100. Alternatively, the elastic members can extend the entire length of the diaper 100, or any other length suitable to provide an elastically contractible line. The length of the elastic members is dictated by the diaper design.

The elastic members can be in a multitude of configurations. For example, the width of the elastic members can be varied from about 0.25 millimeters (0.01 inches) to about 25 millimeters (1.0 inch) or more; the elastic members can comprise a single strand of elastic material or can comprise several parallel or nonparallel strands of elastic material; or the elastic members can be rectangular or curvilinear. Still further, the elastic members can be affixed to the diaper in any of several ways which are known in the art. For example, the elastic members can be ultrasonically bonded, heat and pressure sealed into the diaper 100 using a variety of bonding patterns or the elastic members can simply be glued to the diaper 100.

The absorbent core 106 of the diaper 100 is positioned between the topsheet 104 and the backsheet 102. The absorbent core 106 can be manufactured in a wide variety of sizes and shapes (e.g., rectangular, hourglass, asymmetrical, etc.). The total absorbent capacity of the absorbent core 106 should, however, be compatible with the design liquid loading for the intended use of the absorbent article or diaper. Further, the size and absorbent capacity of the absorbent core 106 can vary to accommodate wearers ranging from infants through adults.

As shown in FIG. 2, the absorbent core 106 includes a fluid distribution member 108 according to the present invention. In a preferred configuration such as depicted in FIG. 2, the absorbent core 106 preferably further includes an acquisition layer or member 110 in fluid communication with the fluid distribution member 108 and located between the fluid distribution member 108 and the topsheet 104. The acquisition layer or member 110 may be comprised of several different materials including nonwoven or woven webs of synthetic fibers including polyester, polypropylene, or polyethylene, natural fibers including cotton or cellulose, blends of such fibers, or any equivalent materials or combinations of materials.

In use, the diaper 100 is applied to a wearer by positioning the back waistband region under the wearer's back, and drawing the reminder of the diaper 100 between the wearer's legs so that the front waistband region is positioned across the front of the wearer. The tape-tab or other fasteners are then secured preferably to outwardly facing areas of the diaper 100. In use, disposable diapers or other absorbent articles incorporating the fluid distribution members of the present invention tend to more quickly and efficiently distribute and store liquids and to remain dry due to the high absorbent capacity of the fluid distribution members. Disposable diapers incorporating the fluid distribution members of the present invention can also be thinner and more flexible.

The specific composition, basis weight, and density characteristics of fluid distribution members according to the present invention are tailored to meet the requirements of a specific absorbent article or product application. Important product parameters which should be considered in selecting a specific fluid distribution member material include: the overall size of the absorbent article; the volume of fluid the product must absorb; and the characteristics of the fluid to be absorbed. Other considerations may be important depending upon the specific product or absorbent article application.

Useful composition ranges for the constituent components are discussed in greater detail hereinabove. Exemplary basis weights and densities of materials which have proven suitable for use in absorbent articles include materials having basis weights of between about 15 and about 350 gsm and densities of between about 0.03 and about 0.20 g/cc. Density may be calculated from the basis weight and the caliper as measured under a given confining pressure, such as 0.20 psi, utilizing the formula:

$$\text{Density (g/cc)} = \text{Basis weight (gsm)}/[10,000 \times \text{Caliper (cm)}]$$

Fluid distribution members according to the present invention may also deviate from a homogeneous profile, density, basis weight, and/or composition. Accordingly, depending upon the particular application it may be desirable to establish gradients in any given direction or directions within the member.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent member for distribution and storage of bodily fluids, said absorbent member comprising:
   (a) between about 20% and about 80% chemically stiffened, twisted, and curled bulking fibers;
   (b) between about 10% and about 80% eucalyptus high surface area fibers; and
   (c) between about 0% and about 50% thermoplastic binding fibers.

2. The absorbent member of claim 1, wherein said absorbent member comprises between about 45% and about 60% chemically stiffened, twisted, and curled bulking fibers.

3. The absorbent member of claim 1, wherein said absorbent member comprises between about 30% and about 45% eucalyptus high surface area fibers.

4. The absorbent member of claim 1, wherein said absorbent member comprises between about 5% and about 15% thermoplastic binding fibers.

5. The absorbent member of claim 1, wherein said absorbent member comprises about 45% chemically stiffened, twisted, and cured cellulosic fibers, about 45% eucalyptus high surface area fibers, and about 10% thermoplastic binding fibers.

6. The absorbent member of claim 1, wherein said thermoplastic binding fibers comprise thermoplastic bicomponent binding fibers.

7. The absorbent member of claim 1, wherein said absorbent member comprises a wetlaid web.

8. The absorbent member of claim 1, wherein said eucalyptus high surface area fibers comprise eucalyptus grandis high surface area fibers.

9. The absorbent member of claim 1, wherein said absorbent member is mechanically softened.

10. An absorbent structure for distribution and storage of bodily fluids, said absorbent structure comprising:
    (a) a fluid acquisition member; and
    (b) a fluid distribution member, said fluid distribution member comprising:
        (i) between about 20% and about 80% chemically stiffened, twisted, and curled bulking fibers;
        (ii) between about 10% and about 80% eucalyptus high surface area fibers; and
        (iii) between about 0% and about 50% thermoplastic binding fibers.

11. The absorbent structure of claim 10, wherein said fluid distribution member comprises between about 45% and about 60% chemically stiffened, twisted, and curled bulking fibers.

12. The absorbent structure of claim 10, wherein said fluid distribution member comprises between about 30% and about 45% eucalyptus high surface area fibers.

13. The absorbent structure of claim 10, wherein said fluid distribution member comprises between about 5% and about 15% thermoplastic binding fibers.

14. The absorbent structure of claim 10, wherein said absorbent structure further includes a second fluid distribution member, said second fluid distribution member comprising:
    (a) between about 20% and about 80% chemically stiffened, twisted, and curled bulking fibers;
    (b) between about 10% and about 80% eucalyptus high surface area fibers; and
    (c) between about 0% and about 50% thermoplastic binding fibers.

15. The absorbent structure of claim 14, wherein said fluid distribution member and said second fluid distribution member have diverse compositions.

16. An absorbent article capable of acquiring, distributing, and storing bodily fluids, said absorbent article comprising:
    (a) a topsheet;
    (b) a backsheet; and
    (c) an absorbent structure located between said topsheet and said backsheet, said absorbent structure including a fluid distribution member, said fluid distribution member comprising;
        (i) between about 20% and about 80% chemically stiffened, twisted, and curled bulking fibers;
        (ii) between about 10% and about 80% eucalyptus high surface area fibers; and
        (iii) between about 0% and about 50% thermoplastic binding fibers.

17. The absorbent article of claim 16, wherein said absorbent article comprises a diaper.

18. The absorbent article of claim 16, wherein said absorbent article comprises a catamenial pad.

19. A method of manufacturing an absorbent member for distribution and storage of bodily fluids, said method comprising:
    (a) forming a blend of fibrous material comprising:
        (i) between about 20% and about 80% chemically stiffened, twisted, and curled bulking fibers;
        (ii) between about 10% and about 80% eucalyptus high surface area fibers; and
        (iii) between about 0% and about 50% thermoplastic binding fibers;
    (b) thermally bonding said thermoplastic fibers.

20. The method of claim 19, wherein said forming step comprises a wetlaying process.

* * * * *

UNITED STATES PATENT AND TRADEMARK OFFICE
CERTIFICATE OF CORRECTION

PATENT NO. : 5,549,589
DATED : August 27, 1996
INVENTOR(S) : James C. Horney, et al.

It is certified that error appears in the above-identified patent and that said Letters Patent is hereby corrected as shown below:

On the title page, item [56], under the section entitled "Foreign Patent Documents", "0618239" should read --0618329--.

In Col. 5, line 46, "twist/cuff" should read --twist/curl--.

In Col. 9, line 39 (appears to be line 37 compared with the PTO line numbers as printed on the patent), "cured" should read --curled--.

In Col. 16, line 18, "deafly" should read --clearly--.

In Col. 17, line 13, "rail" should read --mil--.

In Col. 17, line 55, "comers" should read --corners--.

In Col. 19, line 56, "cured" should read --curled--.

Signed and Sealed this

Third Day of December, 1996

Attest:

BRUCE LEHMAN

*Attesting Officer*   *Commissioner of Patents and Trademarks*